US012599298B2

(12) United States Patent
Halderman et al.

(10) Patent No.: US 12,599,298 B2
(45) Date of Patent: Apr. 14, 2026

(54) SYSTEMS AND METHODS FOR DETECTING PHYSICAL CONTACT OF A SURGICAL INSTRUMENT WITH PATIENT TISSUE

(71) Applicant: Intuitive Surgical Operations, Inc., Sunnyvale, CA (US)

(72) Inventors: Jonathan D. Halderman, Sunnyvale, CA (US); Kayla K. Anderson, Campbell, CA (US); Anqi Fan, Sunnyvale, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 742 days.

(21) Appl. No.: 17/636,121

(22) PCT Filed: Aug. 20, 2020

(86) PCT No.: PCT/US2020/047175
§ 371 (c)(1),
(2) Date: Feb. 17, 2022

(87) PCT Pub. No.: WO2021/035039
PCT Pub. Date: Feb. 25, 2021

(65) Prior Publication Data
US 2022/0287643 A1 Sep. 15, 2022

Related U.S. Application Data

(60) Provisional application No. 62/890,536, filed on Aug. 22, 2019.

(51) Int. Cl.
*A61B 1/12* (2006.01)
*A61B 1/00* (2006.01)
(Continued)

(52) U.S. Cl.
CPC .......... *A61B 1/128* (2013.01); *A61B 1/00006* (2013.01); *A61B 1/00045* (2013.01);
(Continued)

(58) Field of Classification Search
CPC . A61B 1/128; A61B 1/00097; A61B 1/00055; A61B 1/0655; A61B 1/00006; A61B 1/00045; A61B 1/06; A61B 5/6886
See application file for complete search history.

(56) References Cited

U.S. PATENT DOCUMENTS 5,647,840 A * 7/1997 D'Amelio .......... A61B 1/00091
600/176
7,938,774 B2 * 5/2011 Segawa .................. A61B 1/051
600/103
(Continued)

FOREIGN PATENT DOCUMENTS

CN      102106752 A    6/2011
EP       2338431 A1    6/2011
(Continued)

OTHER PUBLICATIONS

International Search Report and Written Opinion for Application No. PCT/US2020/047175, mailed Nov. 26, 2020, 11 pages.
(Continued)

*Primary Examiner* — Ryan N Henderson

(57) ABSTRACT
A tissue contact detection system tracks, over time during a surgical procedure, a temperature of a surgical instrument associated with a surgical system used for the surgical procedure. The system determines, based on the tracked temperature of the surgical instrument, that the temperature of the surgical instrument changes from a first temperature to a second temperature that varies from the first temperature by at least a predetermined amount, and determines, based on the determination that the temperature of the surgical instrument changes from the first temperature to the second
(Continued)

Instrument is in contact with tissue temperature, that the surgical instrument is in physical contact with patient tissue. The system performs, in response to the determination that the surgical instrument is in physical contact with patient tissue, a mitigation operation configured to mitigate the physical contact of the surgical instrument with the patient tissue.

17 Claims, 9 Drawing Sheets

(51) Int. Cl.
    *A61B 1/06*              (2006.01)
    *A61B 5/00*              (2006.01)

(52) U.S. Cl.
    CPC ...... *A61B 1/00055* (2013.01); *A61B 1/00097* (2022.02); *A61B 1/06* (2013.01); *A61B 1/0655* (2022.02); *A61B 5/6886* (2013.01)

(56) References Cited

U.S. PATENT DOCUMENTS

| | | | | | |
|---|---|---|---|---|---|
| 9,642,516 | B2 * | 5/2017 | Yasue | .................... | A61B 1/127 |
| 10,111,581 | B2 * | 10/2018 | Makmel | ................ | A61B 1/253 |
| 10,537,236 | B2 * | 1/2020 | Bennett | .................. | A61B 1/128 |
| 11,686,995 | B2 * | 6/2023 | Halderman | ............ | A61B 1/127 |
| | | | | | 600/169 |
| 2002/0013512 | A1 * | 1/2002 | Sendai | ................. | A61B 5/0084 |
| | | | | | 600/118 |
| 2004/0176683 | A1 * | 9/2004 | Whitin | ................... | A61B 5/068 |
| | | | | | 600/117 |
| 2008/0058602 | A1 * | 3/2008 | Landry | ............... | A61B 1/0655 |
| | | | | | 600/118 |
| 2010/0030020 | A1 * | 2/2010 | Sanders | ................... | A61B 1/04 |
| | | | | | 600/109 |
| 2011/0152854 | A1 * | 6/2011 | Govari | .............. | A61B 18/1492 |
| | | | | | 606/33 |
| 2011/0230906 | A1 * | 9/2011 | Modesitt | ................. | A61B 1/04 |
| | | | | | 606/185 |
| 2011/0319714 | A1 * | 12/2011 | Roelle | ................. | A61B 1/0051 |
| | | | | | 600/118 |
| 2012/0167882 | A1 | 7/2012 | Wood et al. | | |
| 2014/0100421 | A1 * | 4/2014 | Dejima | ................ | A61B 1/0669 |
| | | | | | 600/101 |
| 2014/0200406 | A1 * | 7/2014 | Bennett | ................ | A61B 1/0646 |
| | | | | | 600/109 |
| 2014/0221743 | A1 * | 8/2014 | Sugiyama | ............ | A61B 1/0676 |
| | | | | | 600/109 |
| 2015/0238072 | A1 * | 8/2015 | Makmel | ................. | A61B 1/128 |
| | | | | | 219/221 |
| 2016/0081541 | A1 * | 3/2016 | Yasue | ............... | G02B 23/2476 |
| | | | | | 600/169 |
| 2016/0081555 | A1 * | 3/2016 | Beeckler | ........... | A61B 18/1492 |
| | | | | | 600/478 |
| 2017/0095297 | A1 * | 4/2017 | Richmond | ......... | A61B 1/00006 |
| 2017/0188802 | A1 * | 7/2017 | Lawrence | ........... | A61B 1/0607 |
| 2017/0311789 | A1 * | 11/2017 | Mulcahey | ............. | A61B 1/126 |
| 2017/0354475 | A1 | 12/2017 | Allison et al. | | |
| 2020/0077878 | A1 * | 3/2020 | Halderman | ......... | A61B 1/0008 |
| 2021/0298852 | A1 * | 9/2021 | Crosetti | ................ | A61B 34/76 |

FOREIGN PATENT DOCUMENTS

| | | |
|---|---|---|
| JP | H02106714 A | 4/1990 |
| WO | WO-2016090175 A1 | 6/2016 |
| WO | WO-2018071821 A1 | 4/2018 |

OTHER PUBLICATIONS

Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

International Preliminary Report on Patentability for Application No. PCT/US2020/047175, mailed Mar. 3, 2022, 8 pages.

Extended European Search Report for Application No. EP24202336.4, mailed on Dec. 12, 2024, 06 pages.

* cited by examiner

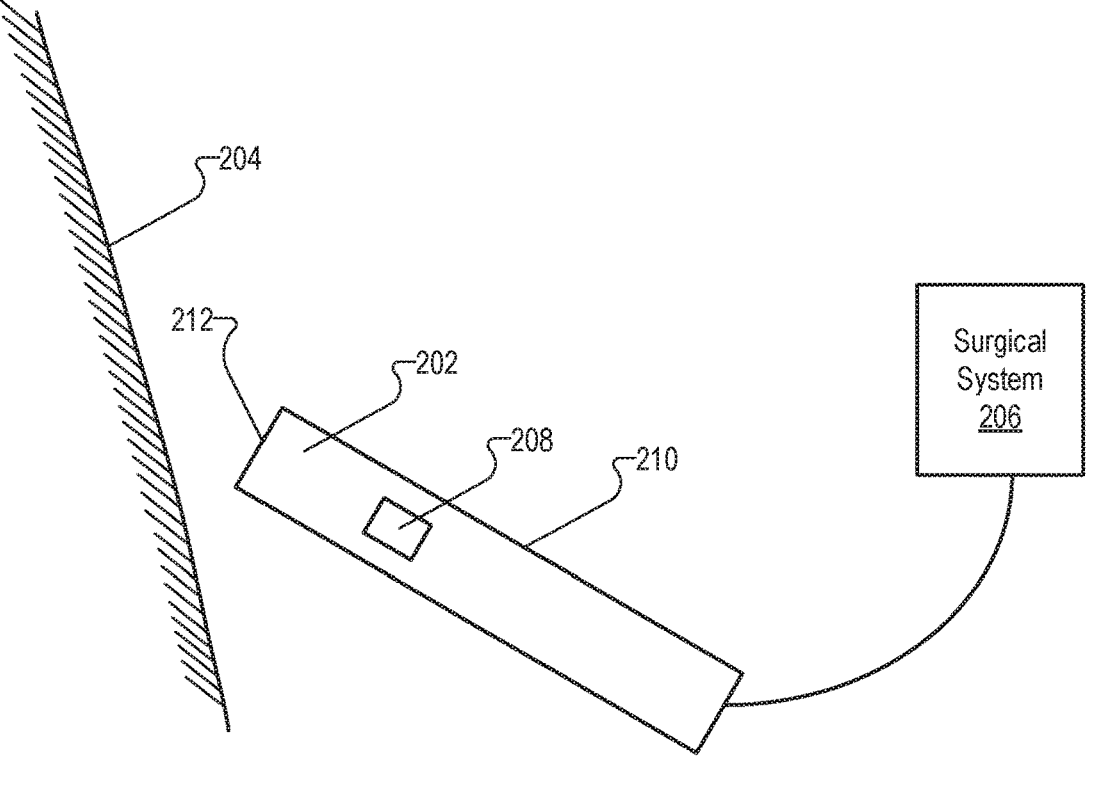
Fig. 2
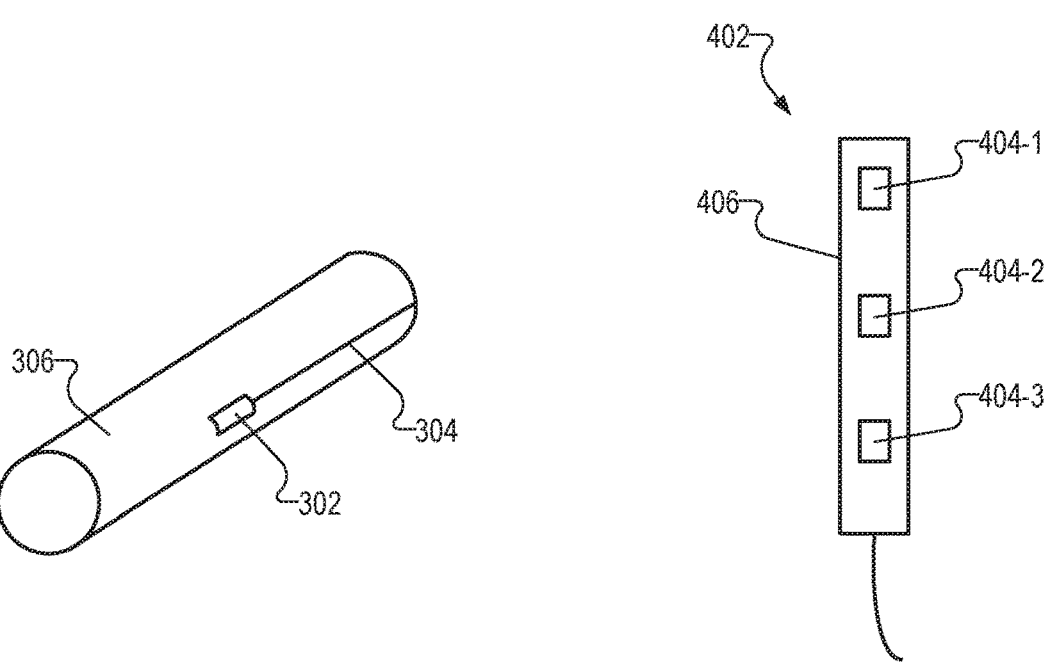
Fig. 3                  Fig. 4

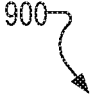
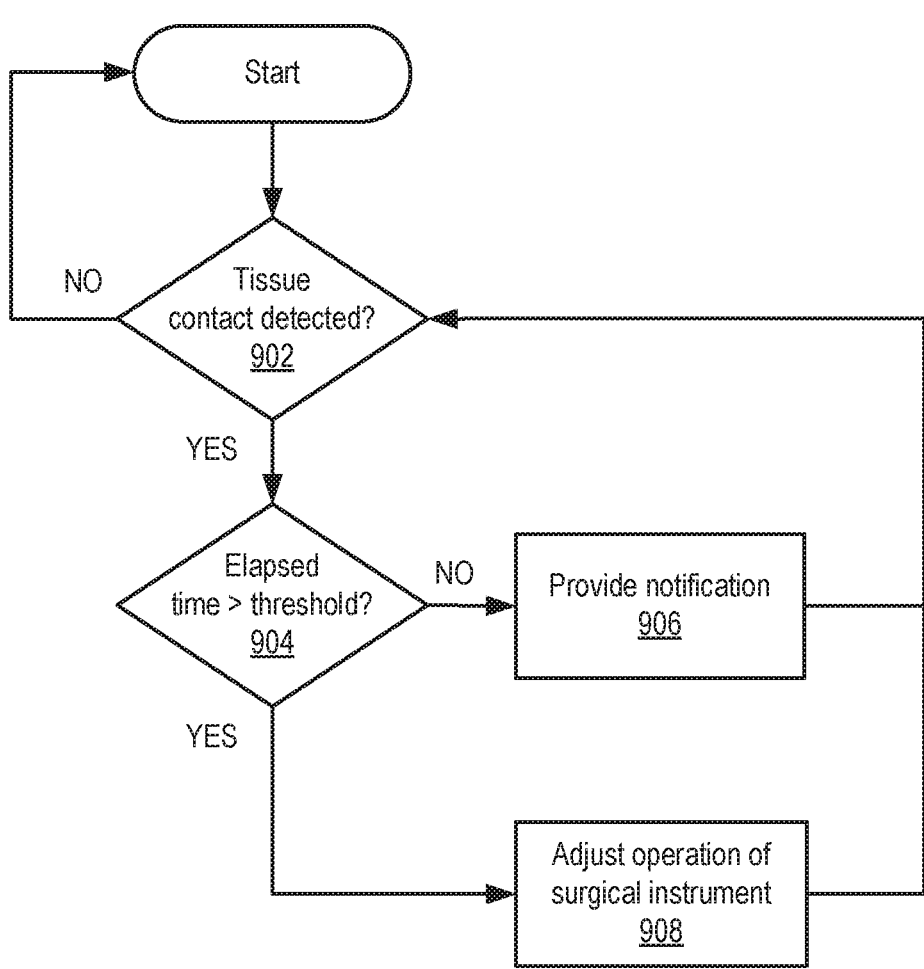
Fig. 9

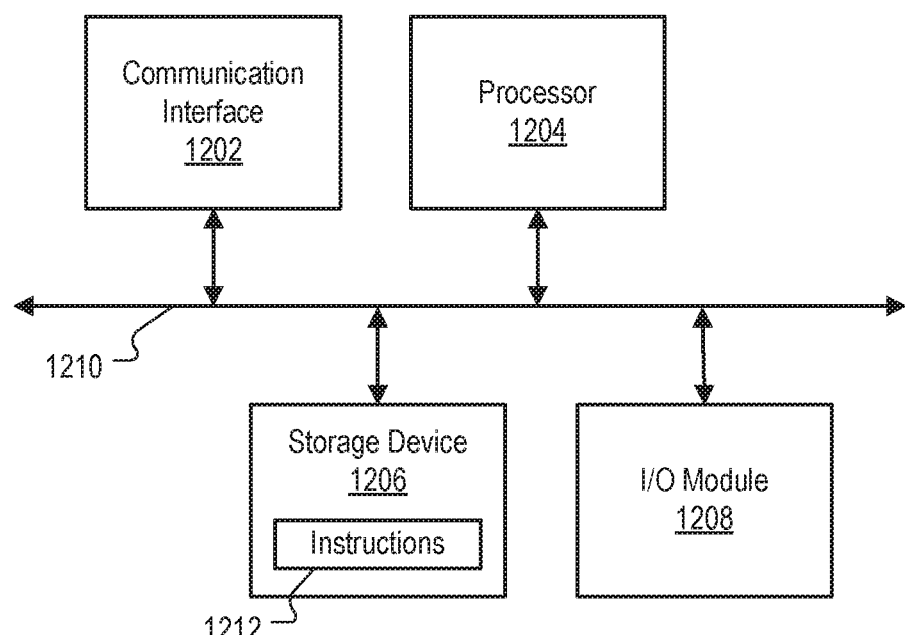
Fig. 12

SYSTEMS AND METHODS FOR DETECTING PHYSICAL CONTACT OF A SURGICAL INSTRUMENT WITH PATIENT TISSUE

RELATED APPLICATIONS

The present application is a U.S. National Stage Application under 35 U.S.C. § 371 of International Application No. PCT/US2020/047175, filed on Aug. 20, 2020, which claims priority to U.S. Provisional Patent Application No. 62/890,536, filed on Aug. 22, 2019, the contents of which are hereby incorporated by reference in their entirety.

BACKGROUND INFORMATION

A surgical instrument that is in physical contact with patient tissue for a prolonged period of time may injure the patient tissue. For example, a surgical instrument that operates at a higher temperature than patient tissue (e.g., an endoscope) may burn the patient tissue after prolonged contact. As another example, a surgical instrument may damage delicate tissue after prolonged contact.

However, in some situations it may be difficult for a surgeon to determine when a surgical instrument is in physical contact with patient tissue. For example, during a minimally-invasive surgical procedure a surgeon may be unable to determine from an endoscopic view of a surgical site when a surgical instrument is in physical contact with patient tissue at or near the surgical site.

SUMMARY

The following description presents a simplified summary of one or more aspects of the methods and systems described herein in order to provide a basic understanding of such aspects. This summary is not an extensive overview of all contemplated aspects, and is intended to neither identify key or critical elements of all aspects nor delineate the scope of any or all aspects. Its sole purpose is to present some concepts of one or more aspects of the methods and systems described herein in a simplified form as a prelude to the more detailed description that is presented below.

An exemplary system may comprise a memory storing instructions and a processor communicatively coupled to the memory and configured to execute the instructions to track, over time during a surgical procedure, a temperature of a surgical instrument associated with a surgical system used for the surgical procedure; determine, based on the tracked temperature of the surgical instrument, that the temperature of the surgical instrument changes from a first temperature to a second temperature that varies from the first temperature by at least a predetermined amount; determine, based on the determination that the temperature of the surgical instrument changes from the first temperature to the second temperature, that the surgical instrument is in physical contact with patient tissue; and perform, in response to the determination that the surgical instrument is in physical contact with patient tissue, a mitigation operation configured to mitigate the physical contact of the surgical instrument with the patient tissue.

Another exemplary system may comprise a temperature sensor configured to detect, during a surgical session, a temperature of a surgical instrument included in a surgical system used for the surgical session; and a processor communicatively coupled to the temperature sensor and configured to execute instructions to track, over time during the surgical session, the temperature of the surgical instrument detected by the temperature sensor; determine, based on the tracked temperature of the surgical instrument, that the temperature of the surgical instrument changes from a first temperature to a second temperature that varies from the first temperature by at least a predetermined amount; determine, based on the determination that the temperature of the surgical instrument changes from the first temperature to the second temperature, that the surgical instrument is in physical contact with patient tissue; and perform, in response to the determination that the surgical instrument is in physical contact with patient tissue, a mitigation operation configured to mitigate the physical contact of the surgical instrument with the patient tissue.

An exemplary method may comprise tracking, by a tissue contact detection system over time during a surgical session, a temperature of a surgical instrument included in a surgical system used for the surgical session; determining, by the tissue contact detection system based on the tracked temperature of the surgical instrument, that the temperature of the surgical instrument changes from a first temperature to a second temperature that varies from the first temperature by at least a predetermined amount; determining, by the tissue contact detection system based on the determination that the temperature of the surgical instrument changes from the first temperature to the second temperature, that the surgical instrument is in physical contact with patient tissue; and performing, by the tissue contact detection system in response to the determination that the surgical instrument is in physical contact with patient tissue, a mitigation operation configured to mitigate the physical contact of the surgical instrument with the patient tissue

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

FIG. 2 illustrates a functional diagram of an exemplary environment in which a surgical procedure is performed according to principles described herein.

FIG. 3 illustrates an exemplary sleeve for use with a surgical instrument according to principles described herein.

FIG. 4 illustrates an exemplary surgical instrument having multiple temperature sensors according to principles described herein.

FIG. 9 illustrates an exemplary method of performing mitigation operations according to principles described herein.

FIG. 12 illustrates an exemplary computing device according to principles described herein.

DETAILED DESCRIPTION

Figure 1:
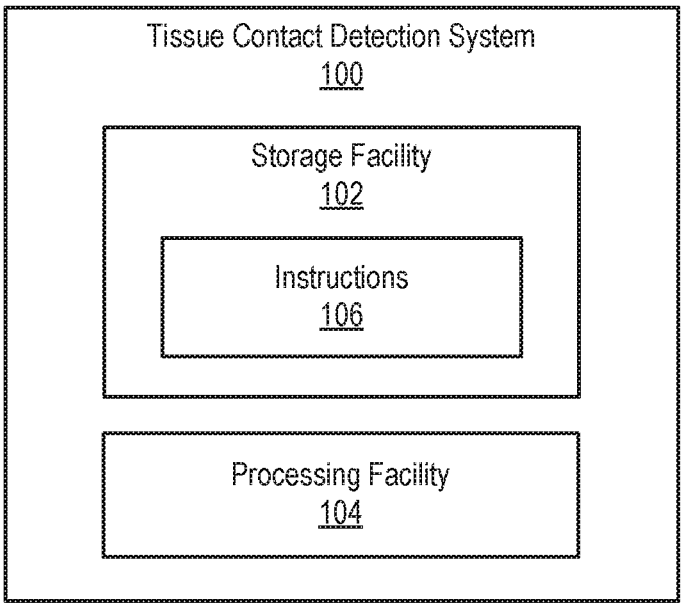
FIG. 1 illustrates an exemplary tissue contact detection system according to principles described herein.

Tissue contact detection systems and methods are described herein. As will be described below in more detail, a tissue contact detection system may track, over time during a surgical session, a temperature of a surgical instrument included in a surgical system used for the surgical session. Based on the tracked temperature of the surgical instrument, the tissue contact detection system may determine that the temperature of the surgical instrument changes from a first temperature to a second temperature that varies from the first temperature by at least a predetermined amount. Based on the determination that the temperature of the surgical instrument changes from the first temperature to the second temperature, the tissue contact detection system may determine that the surgical instrument is in physical contact with patient tissue. In response to the determination that the surgical instrument is in physical contact with patient tissue, the tissue contact detection system may perform a mitigation operation configured to mitigate the physical contact of the surgical instrument with the patient tissue.

To illustrate, during a minimally-invasive surgical procedure an endoscope included in a computer-assisted surgical system may be used to illuminate a surgical area within a patient and provide images of the surgical area for display and use by a surgeon in performing the surgical procedure. During the surgical procedure the endoscope may operate at a temperature (e.g., 50° C.) that is higher than a nominal temperature of patient tissue (e.g., 37° C.). When a shaft of the endoscope physically contacts the patient tissue, the patient tissue acts as a conductive heat sink and the temperature of the endoscope drops (e.g., decreases from 50° C. to 47° C.).

During the surgical session a tissue contact detection system may track, over time, the temperature of the endoscope and determine that the temperature of the endoscope changes (e.g., decreases from 50° C. to 47° C.). The tissue contact detection system may determine that this temperature change exceeds at least a predetermined amount (e.g., 2° C.) and thus determine that the endoscope is in physical contact with patient tissue. To mitigate the physical contact of the surgical instrument with the patient tissue the tissue contact detection system may present, or direct the surgical system to present, a notification (e.g., a visual notification, a warning message, an audible notification, etc.) of the physical contact of the surgical instrument with the patient tissue. The surgeon may respond to the notification by removing the endoscope from the physical contact with the patient tissue. Additionally or alternatively, the tissue contact detection system may decrease, or direct the surgical system to decrease, an intensity of illumination emitted from the endoscope and/or turn off auxiliary illumination (e.g., fluorescence excitation illumination).

The systems and methods described herein may provide various benefits. For example, the systems and methods described herein may reduce the risk of injury to patient tissue caused by prolonged physical contact with a surgical instrument. Additionally, the determination that the surgical instrument is in physical contact with patient tissue is highly reliable because it is based on a detected temperature change of the surgical instrument, which change is detectable, has low noise, and is not affected by electrical noise in the operating environment. Furthermore, the systems and methods described herein enable detection of physical contact by a surgical instrument with patient tissue located outside of an endoscopic view. These and other benefits of the systems and methods described herein will be made apparent in the description that follows.

FIG. 1 illustrates an exemplary tissue contact detection system 100 ("system 100") that may be configured to determine that a surgical instrument is in physical contact with patient tissue. System 100 may be included in, implemented by, or connected to any surgical systems or other computing systems described herein. For example, system 100 may be implemented by a computer-assisted surgical system. As another example, system 100 may be implemented by a stand-alone computing system communicatively coupled to a computer-assisted surgical system.

As shown, system 100 includes, without limitation, a storage facility 102 and a processing facility 104 selectively and communicatively coupled to one another. Facilities 102 and 104 may each include or be implemented by hardware and/or software components (e.g., processors, memories, communication interfaces, instructions stored in memory for execution by the processors, etc.). For example, facilities 102 and 104 may be implemented by any component in a computer-assisted surgical system. In some examples, facilities 102 and 104 may be distributed between multiple devices and/or multiple locations as may serve a particular implementation.

Storage facility 102 may maintain (e.g., store) executable data used by processing facility 104 to perform any of the operations described herein. For example, storage facility 102 may store instructions 106 that may be executed by processing facility 104 to perform any of the operations described herein. Instructions 106 may be implemented by any suitable application, software, code, and/or other executable data instance. Storage facility 102 may also maintain any data received, generated, managed, used, and/or transmitted by processing facility 104.

Processing facility 104 may be configured to perform (e.g., execute instructions 106 stored in storage facility 102 to perform) various operations associated with detecting that a surgical instrument is in physical contact with patient tissue. For example, processing facility 104 may be configured to track, over time during a surgical session, a temperature of a surgical instrument included in a surgical system used for the surgical session. Based on the tracked temperature of the surgical instrument, processing facility 104 may determine that the temperature of the surgical instrument changes from a first temperature to a second temperature that varies from the first temperature by at least a predetermined amount. Based on the determination that the temperature of the surgical instrument changes from the first temperature to the second temperature, processing facility 104 may determine that the surgical instrument is in physical contact with patient tissue. In response to the determination that the surgical instrument is in physical contact with patient tissue, processing facility 104 may perform, or direct the surgical system to perform, a mitigation operation configured to mitigate the physical contact of the surgical instrument with the patient tissue. These and other operations that may be performed by processing facility 104 are described herein. In the description that follows, any references to operations performed by system 100 may be understood to be performed by processing facility 104 of system 100.

As mentioned, system 100 may be configured to track, over time during a surgical procedure, a temperature of a surgical instrument used in the surgical procedure. FIG. 2 illustrates a functional diagram of an exemplary environment in which a surgical procedure is performed. As shown, a surgical instrument 202 is used during a surgical procedure to perform one or more operations with respect to a patient. As a result, surgical instrument 202 may at various times be positioned near patient tissue 204 located at a surgical area associated with the patient. A surgical procedure may include any procedure in which manual and/or instrumental techniques are used to perform operations on a patient to investigate, diagnose, and/or treat a physical condition of the patient. For example, surgical instrument 202 may be used to perform a minimally invasive surgical procedure on tissue internal to a patient. In other examples, surgical instrument 202 may be used to perform an open surgical procedure, such as when part of the surgical area (e.g., tissue being operated on) is internal to the patient while another part of the surgical area (e.g., a space around the tissue where one or more surgical instruments may be disposed) is external to the patient.

Surgical instrument 202 may be implemented by any suitable surgical tool (e.g., a tool having tissue-interaction functions), medical tool, monitoring instrument (e.g., an endoscope), sensing instrument (e.g., a force-sensing surgical instrument), diagnostic instrument, or the like that may be used for a surgical procedure (e.g., a computer-assisted surgical procedure in which the surgical instrument is at least partially inserted into a patient and manipulated to perform a minimally-invasive surgical procedure on the patient). Surgical instrument 202 is associated with (e.g., connected to, integrated into, or implemented by) a surgical system 206. In some examples surgical system 206 is connected to, integrated into, or implemented by a computer-assisted surgical system that utilizes robotic and/or teleoperation technology to control surgical instrument 202 to perform a surgical procedure (e.g., a minimally invasive surgical procedure). An exemplary computer-assisted surgical system is described below in more detail. In some examples system 100 is implemented entirely by surgical instrument 202 and/or surgical system 206. As another example, system 100 may be implemented, in whole or in part, by a stand-alone computing system communicatively coupled to surgical instrument 202 and/or surgical system 206 (e.g., by way of a network).

Surgical instrument 202 includes a temperature sensor 208 configured to measure a temperature of surgical instrument 202. Temperature sensor 208 may implemented by any suitable temperature sensing device, such as but not limited to a thermocouple, a resistance thermometer, a thermistor, a semiconductor-based temperature sensor, a fiber optic temperature probe, and the like. In some examples temperature sensor 208 may be connected to, integrated with, or included in system 100.

Temperature sensor 208 may be positioned at any position on surgical instrument 202 as may suit a particular implementation. In some examples, as shown in FIG. 2, temperature sensor 208 is positioned on a shaft wall 210 of surgical instrument 202. Alternatively, temperature sensor 208 may be positioned on a distal end 212 of surgical instrument 202. In some examples temperature sensor 208 is configured to measure a temperature of an external surface of surgical instrument 202. Accordingly, temperature sensor 208 may be positioned in contact with the external surface of surgical instrument 202. For instance, temperature sensor 208 may be positioned externally on shaft wall 210. In alternative examples, temperature sensor 208 may be positioned internally within surgical instrument 202. In some examples where temperature sensor 208 is not in contact with the external surface of surgical instrument 202, the temperature value measured by temperature sensor 208 may be correlated to a temperature of the external surface of surgical instrument 202.

As shown in FIG. 2, temperature sensor 208 is integrated with surgical instrument 202. For example, temperature sensor 208 is built into surgical instrument 202, and temperature data generated by temperature sensor 208 is transmitted to surgical system 206 by way of surgical instrument 202 (e.g., by wiring located within surgical instrument 202). Alternatively, temperature sensor 208 may be independent of surgical instrument 202. FIG. 3 illustrates an exemplary embodiment in which a temperature sensor is separate from a surgical instrument. As shown, a temperature sensor 302 and wiring 304 are integrated into a sleeve 306. Sleeve 306 is formed of a material having high thermal conductivity, such as a metal, a polymer with thermally-conductive additives, and the like. Sleeve 306 is configured to be positioned on a shaft of a surgical instrument (e.g., around shaft wall 210 of surgical instrument 202). In some examples sleeve 306 is selectively removable from surgical instrument 202. In this way temperature sensor 302 can be used with various different surgical instruments as the need may arise. In other examples sleeve 306 may be permanently secured to surgical instrument 202. Wiring 304 is configured to transmit temperature data to a computing system (e.g., to surgical system 206). Sleeve 306 enables tracking of the temperature of legacy surgical instruments that do not include an integrated temperature sensor. Additionally, sleeve 306 facilitates and improves the tracking of the temperature of surgical instruments having a low thermal conductivity (e.g., surgical instruments having a non-metallic shaft).

In some examples a temperature sensor may be integrated with surgical instrument 202 (e.g., on an exterior surface of shaft wall 210), and a thermally-conductive sleeve (similar to sleeve 306) is provided over surgical instrument 202 to improve the detection of tissue contact.

Referring again to FIG. 2, surgical instrument 202 may include one or more other sensors (not shown), such as displacement transducers, orientational sensors, positional sensors, etc., for generating kinematics information (hereinafter "surgical instrument sensors"). Kinematics information may include information such as pose (e.g., position and/or orientation), movement (e.g., velocity, direction, acceleration, etc.), state (e.g., open, closed, stowed, etc.), and/or other attributes of surgical instrument 202. System 100 and/or surgical system 206 may be configured to use the kinematics information to track (e.g., determine poses, movements, and/or states of) and/or control surgical instrument 202. Surgical instrument 202 may also include other sensors configured to generate other information as may suit a particular implementation. As will be explained below in more detail, system 100 may also be configured to track, based on parameters sensed by the surgical instrument sensors, operations of surgical instrument 202, and determine whether surgical instrument 202 is in physical contact with patient tissue 204 based on the tracked operations.

The foregoing embodiments have described use of a single temperature sensor. In alternative embodiments surgical instrument 202 and/or sleeve 306 may include a plurality of temperature sensors configured to measure the temperature of surgical instrument 202 at distinct locations on surgical instrument 202. For example, as shown in FIG. 4 a surgical instrument 402 includes multiple temperature sensors 404 (e.g., temperature sensors 404-1, 404-2, and 404-3) positioned at distinct locations along a shaft 406 of surgical instrument 402. For instance, temperature sensor 404-1 is positioned at about 5 mm from a distal end of surgical instrument 402, temperature sensor 404-2 is positioned at about 25 mm from a distal end of surgical instrument 402, and temperature sensor 404-3 is positioned at about 40 mm from a distal end of surgical instrument 402. While three temperature sensors 404 are shown in FIG. 4, surgical instrument 402 may include fewer or more temperature sensors as may suit a particular implementation. Additionally, temperature sensors 404 may be positioned at any locations on surgical instrument 402 as may suit a particular implementation.

As mentioned above, system 100 may be configured to track the temperature of a surgical instrument (e.g., surgical instrument 202 and/or surgical instrument 402). The tracking may be performed in any suitable way. In some examples the tracking includes collecting and/or storing temperature data representative of a measured temperature of the surgical instrument. For example, system 100 may collect temperature data from a temperature sensor (e.g., temperature sensor 208, temperature sensor 302, and/or a temperature sensor 404) at regular intervals (e.g., every second, every 5 seconds, etc.) and store the collected temperature data (e.g., in storage facility 102). In examples where the surgical instrument includes multiple temperature sensors, the tracking includes collecting and/or storing temperature data for each temperature sensor. In some examples the tracking may also include processing the collected temperature data, such as to remove noise, amplify signals, convert temperature data (e.g., convert a measured temperature value of an internal temperature of surgical instrument 202 to a temperature value of an external surface of surgical instrument 202), generate a temperature profile, and the like.

Figure 5:
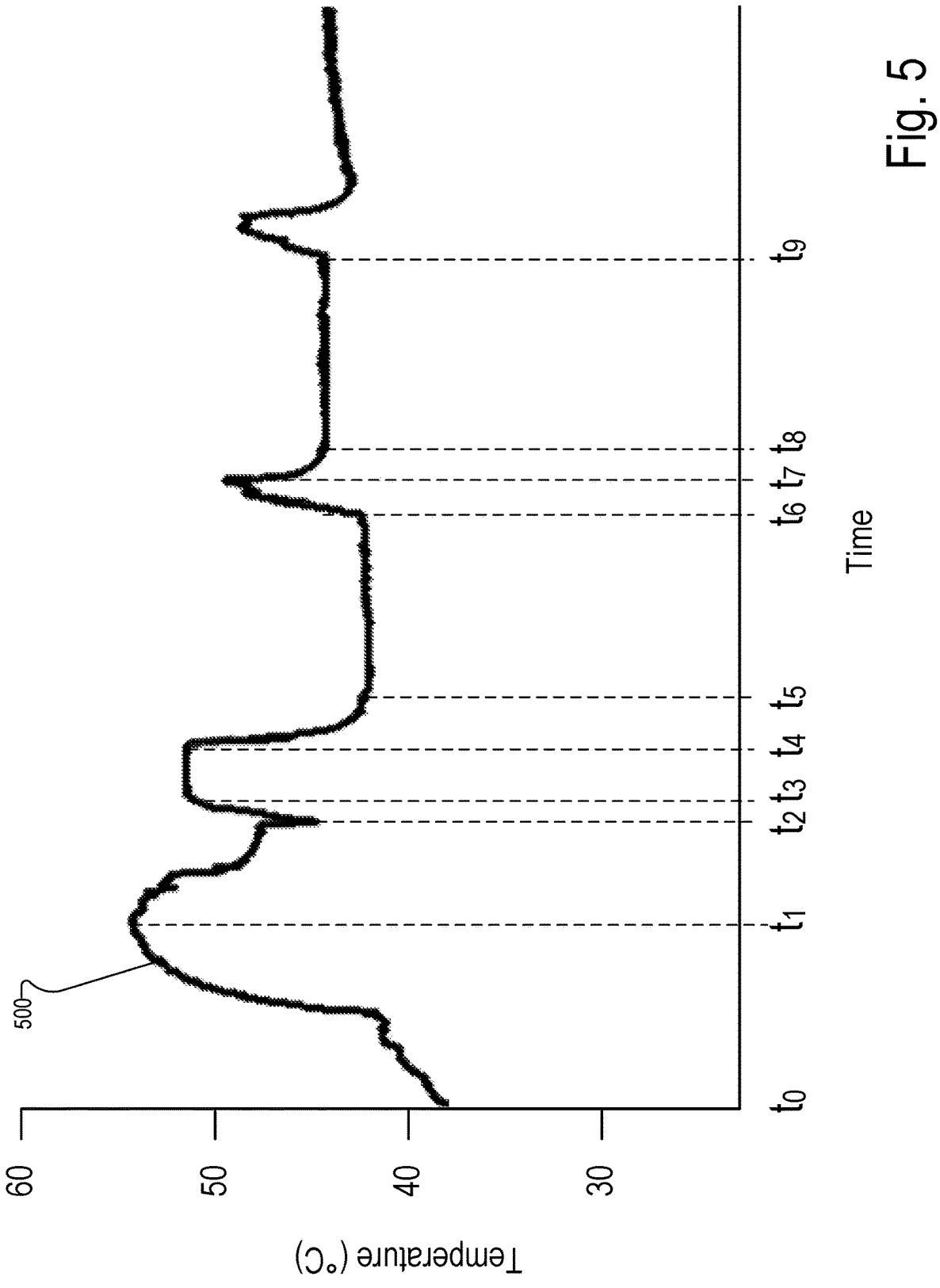
FIG. 5 illustrates an exemplary temperature profile of a surgical instrument based on tracked temperature data according to principles described herein.

Based on the tracked temperature of the surgical instrument, system 100 may detect that the surgical instrument is in physical contact with patient tissue. Various examples of detecting that the surgical instrument is in physical contact with patient tissue based on the tracked temperature of the surgical instrument will now be described with reference to FIG. 5. FIG. 5 illustrates an exemplary temperature profile 500 of a surgical instrument based on the tracked temperature data. Temperature profile 500 plots the tracked temperature of the surgical instrument over time.

In some examples, system 100 is configured to determine that the surgical instrument is in physical contact with patient tissue when system 100 determines that the temperature of the surgical instrument changes from a first temperature to a second temperature that varies from the first temperature by at least a predetermined amount. In some examples the first temperature and/or the second temperature are each an instantaneous temperature value. For instance, the first temperature may be a most recent maximum temperature, such as a maximum temperature occurring during a predetermined time interval (e.g., 5 seconds). Similarly, the second temperature may be a most recent minimum temperature, such as a minimum temperature occurring during the predetermined time interval. Alternatively, the first temperature and/or the second temperature may each be an average of multiple temperature values sampled during a predetermined time interval (e.g., 5 seconds). In yet further examples that will be explained below, the first temperature and/or the second temperature are each a steady-state temperature (e.g., a temperature of the surgical instrument when the temperature of the surgical instrument is in a steady-state).

The predetermined amount may be set in any suitable manner, and is generally set at a value indicative of tissue contact. For example, the predetermined amount may be a predetermined temperature difference value (e.g., 5° C.) or a percentage of the first temperature (e.g., 10%). If the change in temperature is equal to at least the predetermined amount, system 100 determines that the surgical instrument is in physical contact with patient tissue. If, however, the change in temperature is less than the predetermined amount, system 100 does not determine that the surgical instrument is in physical contact with patient tissue.

To illustrate, as shown in FIG. 5 the temperature of the surgical instrument at time $t_1$ is approximately 55.7° C. and at time $t_2$ is approximately 44.5° C. If the predetermined amount is a temperature difference value of 7° C., then system 100 infers that the temperature drop is due to the surgical instrument being in physical contact with patient tissue because the change in temperature is 11.2° C., which is greater than the predetermined temperature difference value of 7° C. Thus, system 100 determines that the surgical instrument is in physical contact with patient tissue at time $t_2$. Similarly, the temperature of the surgical instrument at time $t_4$ is approximately 51.4° C. and at time $t_5$ is approximately 42.0° C. Accordingly, system 100 determines that the surgical instrument is in physical contact with patient tissue at time $t_5$ because the change in temperature is 9.4° C., which is greater than the predetermined temperature difference value of 7° C. On the other hand, the temperature of the surgical instrument at time $t_7$ is approximately 50.0° C. and at time $t_8$ is approximately 44.3° C. Accordingly, system 100 does not determine that the surgical instrument is in physical contact with patient tissue at time $t_8$ because the change in temperature is 5.7° C., which is less than the predetermined temperature difference value of 7° C.

In some examples system 100 determines that the surgical instrument is in physical contact with patient tissue only when the temperature of the surgical instrument changes in a direction toward the temperature of the patient tissue (e.g., nominal body temperature of 37° C.). In other words, if the first temperature of the surgical instrument is greater than the temperature of the patient tissue, then only a decrease in temperature of the surgical instrument (i.e., the second temperature of the surgical instrument is less than the first temperature) will indicate physical contact with patient tissue. On the other hand, if the first temperature of the surgical instrument is less than the temperature of the patient tissue, then only an increase in temperature of the surgical instrument (i.e., the second temperature of the surgical instrument is greater than the first temperature) will indicate physical contact with patient tissue.

In additional or alternative examples system 100 may determine that the surgical instrument is in physical contact with patient tissue based on a determination that the first temperature and/or the second temperature of the surgical instrument is in a steady-state. System 100 may determine that the temperature of the surgical instrument is in a steady-state in any suitable way. In some examples the temperature of the surgical instrument is in a steady-state when the temperature of the surgical instrument does not vary by more than a predetermined steady-state amount over a predetermined steady-state time period. The predetermined steady-state amount may be any suitable amount and may be specified as a temperature difference value (e.g., ±2° C.) or a percentage (e.g., ±5%). The predetermined steady-state time period may be any suitable time period (e.g., 15 seconds).

To illustrate, as shown in FIG. 5 the surgical instrument is initialized (e.g., connected to a surgical system, docked, turned on, first operated, etc.) at time $t_0$ and operates in an initialization phase from time $t_0$ to time $t_3$. During the initialization phase the temperature of the surgical instrument ramps-up and fluctuates (e.g., due to manual handling of the surgical instrument, navigation of the surgical instrument to a surgical area within the patient, activation of optical illumination, movement of the surgical instrument, etc.). Thus, the temperature of the surgical instrument does not reach a steady-state between time $t_0$ and time $t_3$. Accordingly, although the temperature change from time $t_1$ to time $t_2$ may be greater than the predetermined amount, system 100 does not determine that the surgical instrument is in physical contact with patient tissue because the temperature of the surgical instrument has not reached a steady state. However, the temperature of the surgical instrument reaches a steady-state between time $t_3$ to time $t_4$ and between time $t_5$ to time $t_6$. Thus, system 100 may determine that the surgical instrument is in physical contact with patient tissue between time $t_5$ to time $t_6$ if the second temperature varies from the first temperature by at least the predetermined amount.

In some examples the determination that the surgical instrument is in physical contact with patient tissue is conditioned at least on the second temperature of the surgical instrument being in a steady-state. For instance, system 100 does not determine that the surgical instrument is in physical contact with patient tissue at any time between time $t_1$ and time $t_3$ because the temperature of the surgical instrument is not in a steady-state. On the other hand, provided that the second temperature varies from the first temperature by at least the predetermined amount, system 100 determines that the surgical instrument is in physical contact with patient tissue between time $t_5$ and $t_6$ because the temperature of the surgical instrument is in a steady-state from time $t_5$ to time $t_6$.

In additional or alternative examples the determination that the surgical instrument is in physical contact with patient tissue is conditioned at least on the first temperature of the surgical instrument being in a steady-state. For instance, system 100 does not determine that the surgical instrument is in physical contact with patient tissue at any time between time $t_0$ and time $t_3$ because the temperature of the surgical instrument is not in a steady-state. On the other hand, provided that the second temperature varies from the first temperature by at least the predetermined amount, system 100 determines that the surgical instrument is in physical contact with patient tissue between time $t_5$ and $t_6$ because the temperature of the surgical instrument is in a steady-state from time $t_3$ to time $t_4$.

In some examples the determination that the surgical instrument is in physical contact with patient tissue is based on a determination of a non-contact state temperature of the surgical instrument. A non-contact state temperature is a normal operating temperature of the surgical instrument when the surgical instrument is not in contact with patient tissue. The non-contact state temperature of the surgical instrument may be determined in any suitable way. In some examples the non-contact state temperature may be the first instance of a steady-state temperature during use of the surgical instrument (e.g., the temperature from time $t_3$ to time $t_4$ in FIG. 5). Alternatively, the non-contact state temperature may be predetermined (e.g., based on empirical analysis).

As mentioned, system 100 is configured to determine that the surgical instrument is in physical contact with patient tissue when system 100 determines that the temperature of the surgical instrument changes from a first temperature to a second temperature that varies from the first temperature by at least a predetermined amount. In some examples the non-contact state temperature is set as the first temperature for all real-time determinations of tissue contact during the surgical procedure. To illustrate, system 100 may determine that the first instance of a steady-state temperature occurs from time $t_3$ to time $t_4$ and thus determine that the non-contact state temperature of the surgical instrument is the temperature at time $t_3$ to $t_4$, i.e., approximately 51.4° C. System 100 may set the first temperature to the non-contact state temperature (e.g., 51.4° C.). The temperature of the surgical instrument changes from approximately 50.0° C. at time $t_7$ to approximately 44.3° C. at time $t_8$. If the predetermined amount is set at 7° C., the temperature change from time $t_7$ to time $t_8$ is 5.7° C., which is less than the predetermined amount. However, system 100 determines that the surgical instrument is in physical contact with patient tissue at time $t_8$ because the temperature of the surgical instrument changes from the first temperature (the non-contact state temperature, i.e., 51.4° C.) to a second temperature (approximately 44.3° C. at time $t_8$) that varies from the first temperature by 7.1° C., which is greater than the predetermined amount. In this way physical contact with tissue may be detected even though the surgical instrument may not have completely returned to its non-contact state temperature after a prior decrease in temperature.

In additional or alternative embodiments, system 100 determines whether the surgical instrument is in physical contact with patient tissue based on a detected rate of temperature change. The rate of temperature change may indicate whether the surgical instrument is in physical contact with patient tissue or whether the temperature change is due to some other cause. For example, the surgical instrument may change temperature faster when in physical contact with patient tissue than when in contact with another surgical instrument operating at a temperature above the patient tissue temperature.

System 100 may determine the rate of temperature change in any suitable way. In some examples system 100 determines an average rate of temperature change over a period of time; such as over a regular period of time (e.g.; every 5 seconds), over a period of time between a most recent maximum temperature and a most recent minimum temperature (e.g., between time $t_7$ and time $t_8$), over a period of time between successive steady-state temperatures (e.g., between time $t_4$ and time $t_5$), and the like. System 100 may determine that the surgical instrument is in physical contact with patient tissue if the measured rate of temperature change is greater than or equal to a rate change minimum value (e.g., 1° C./minute), less than or equal to a rate change maximum value (e.g., 3° C./minute), or within a particular rate change range (e.g.; between 1° C./minute and 3° C./minute). The rate change minimum value; maximum value; and/or range may be predetermined (e.g., based on empirical analyses) or it may be set based on the detected non-contact state temperature of the surgical instrument.

To illustrate; as shown in FIG. 5 the temperature change from time $t_1$ to time $t_2$ may be due to initialization of the surgical instrument and/or navigation of the surgical instrument to the surgical area within the patient, while the temperature change from time $t_4$ to time $t_5$ may be due to contact with patient tissue. If the rate change minimum value is 1.0° C./minute, the rate change maximum value is 3.0° C./minute, the rate of temperature change from time $t_1$ to time $t_2$ is 0.9° C./minute, and the rate of temperature change from time $t_4$ to time $t_5$ is 2.0° C./minute, system 100 determines that the surgical instrument is in physical contact with patient tissue at time $t_5$ but not at time $t_2$ because only the rate of temperature change from time $t_4$ to time $t_5$ falls between the rate change minimum and maximum values.

Alternatively to tracking a rate of temperature change, system 100 may determine that the surgical instrument is in physical contact with patient tissue when system 100 determines that the temperature of the surgical instrument changes from a first temperature to a second temperature that varies from the first temperature by at least a predetermined amount within a predetermined time interval. For instance, system 100 may determine that the surgical instrument is in physical contact with patient tissue at time $t_5$ because the temperature change of the surgical instrument from time $t_1$ to time $t_5$ exceeds the predetermined amount of temperature change and the amount of time elapsed from time $t_4$ to time $t_5$ is within the predetermined time interval (e.g., within 30 seconds).

In additional or alternative embodiments, system 100 determines that the surgical instrument is in physical contact with patient tissue if the second temperature is within a contact-state range of a contact-state temperature. The contact-state temperature of the surgical instrument refers to a steady-state temperature of the surgical instrument when the surgical instrument is in contact with patient tissue. Since a temperature of patient tissue is generally constant (approximately 37° C.), the contact-state temperature of the surgical instrument may be measured empirically or calculated or based on the non-contact state temperature of the surgical instrument.

The contact-state range refers to a temperature range within which the temperature of the surgical instrument may vary while the surgical instrument remains in contact with patient tissue, and may be represented as a temperature value (e.g., ±2° C.) or a percentage (e.g., ±5%). For instance, if the non-contact state temperature of the surgical instrument is 51.4° C. (see FIG. 5), system 100 may determine (e.g., calculate or determine from pre-stored data) that the contact state temperature of the surgical instrument is 42° C. Accordingly, system 100 may determine that the surgical instrument is in physical contact with patient tissue if the measured temperature of the surgical instrument is within the contact-state range, e.g., 42° C.±2° C. or 42° C.±5%, as is the case from time $t_5$ to $t_6$ but not from time $t_8$ to $t_9$.

In some cases the non-contact state temperature of the surgical instrument may not be high (or low) enough to generate an easily detectable temperature change when the surgical instrument physically contacts patient tissue. Accordingly, system 100 may be configured to maintain the non-contact state temperature of the surgical instrument at a predetermined level (e.g., at 47° C.), or at such a level that the non-contact state temperature varies from the tissue temperature by at least a predetermined non-contact state difference amount (e.g., 10° C.), such as by passively applying heat to or removing heat from the surgical instrument. The non-contact state temperature of the surgical instrument may be increased or decreased such that the non-contact state temperature of the surgical instrument varies from the temperature of the patient tissue by at least the predetermined non-contact state difference amount. In some examples system 100 is configured to adjust the non-contact state temperature of the surgical instrument in response to a determination that the non-contact state temperature of the surgical instrument varies from the temperature of patient tissue by less than the predetermined non-contact state difference amount. By adjusting the non-contact state temperature of surgical system as just described, system 100 may ensure that physical contact with patient tissue can be accurately detected.

In the foregoing embodiments system 100 determines that the surgical instrument physically contacts patient tissue based on a tracked temperature of the surgical instrument. In the embodiments described above the temperature of the surgical instrument is tracked based on the temperature value measured by a temperature sensor (e.g., temperature sensor 208 or temperature sensor 302) on the surgical instrument. In embodiments where the surgical instrument includes multiple temperature sensors (see, e.g., FIG. 4), the temperature of the surgical instrument is tracked at each location on the surgical instrument where a temperature sensor is located. Accordingly, in some examples system 100 may determine that the surgical instrument physically contacts patient tissue if system 100 determines that, at any one or more of the locations on the surgical instrument, the temperature of the surgical instrument changes from a first temperature to a second temperature that varies from the first temperature by at least the predetermined amount. Moreover, system 100 may determine, based on the tracked temperature at each location on the surgical instrument, the particular location on the surgical instrument that is in physical contact with patient tissue. In alternative examples, system 100 may determine that the surgical instrument physically contacts patient tissue only if system 100 determines that, at two or more of the locations on the surgical instrument, the temperature of the surgical instrument changes from a first temperature to a second temperature that varies from the first temperature by at least the predetermined amount.

In embodiments in which the surgical instrument includes multiple temperature sensors, the sensitivity of the tissue contact detection may also be dependent on the location of the temperature sensors on the surgical instrument. For instance, the predetermined amount may be set to be larger for temperature data obtained from a temperature sensor located close to the distal end of an endoscope (e.g., at 5 mm from the distal end) than for a temperature sensor located farther (e.g., 25 mm) from the distal end.

In the foregoing embodiments system 100 determines that the surgical instrument physically contacts patient tissue based on a tracked temperature of the surgical instrument. In other embodiments, system 100 may determine that the surgical instrument physically contacts patient tissue based also on tracked operations of the surgical instrument. Tracked operations of the surgical instrument may be used by system 100 in conjunction with the tracked temperature of the surgical instrument to better determine when the surgical instrument physically contacts patient tissue.

As used herein, operations of the surgical instrument may include any mechanical, electrical, optical, hardware, and/or software-based operations as may serve a particular implementation. For example, operations of the surgical instrument may include movement of the surgical instrument, operation of a functional feature of the surgical instrument (e.g., energizing a cautery instrument, opening and closing forceps or scissors, firing a stapling instrument, activating fluorescence excitation illumination, etc.), adjustment of a surgical instrument setting (e.g., adjusting an exposure level or a zoom level of an endoscope, etc.), detection of reflected illumination by an image sensor, detection of a system fault or error (e.g., detection of a collision of the surgical instrument with another surgical instrument, etc.), generation of a fault code, and the like.

System 100 may track operations of the surgical instrument in any suitable way. In some examples the tracking includes collecting surgical session data representative of operations of the surgical instrument during a surgical session and/or processing the surgical session data (e.g., to reduce noise, sort and classify events, apply timestamps, etc.). The surgical session data may be generated by system 100, the surgical instrument, a surgical system associated with the surgical instrument, and/or by any other device associated with the surgical instrument as may serve a particular implementation. Surgical session data generated during a surgical session may include various types of data. For example, surgical session data generated during a surgical session may include kinematic data, image data, sensor data, surgical instrument data, and/or any other type of data as may serve a particular implementation.

Kinematic data may be representative of a pose of the surgical instrument, movement of the surgical instrument, and any other positional and/or motion-based information as may suit a particular implementation. Image data may be representative of one or more images captured by the surgical instrument. For example, image data may be representative of one or more still images and/or video captured by an imaging device (e.g., a stereoscopic endoscope). Sensor data may include any data generated by surgical instrument sensors included in or associated with the surgical instrument. Sensor data may be representative of any sensed parameter as may serve a particular implementation. In some examples, certain kinematic data and image data may be generated by and/or based on parameters sensed by surgical system sensors. Accordingly, sensor data may include such kinematic data and image data. Surgical instrument data may include any other data generated or maintained by the surgical instrument, such as an identification ("ID") of the surgical instrument, an operational state of the surgical instrument (e.g., open, closed, electrically charged, idle, etc.), a fault code of the surgical instrument, and the like.

As mentioned, system 100 may be configured to determine that the surgical instrument is in physical contact with patient tissue further based on the tracked operations of the surgical instrument. For example, as shown in FIG. 5 system 100 may determine that the temperature of the surgical instrument changes from a first temperature at time $t_7$ to a second temperature at time $t_8$ that varies from the first temperature by more than a predetermined amount. However, system 100 may further determine, based on the tracked operations of the surgical instrument, that the surgical instrument is an endoscope and that an illumination source that provides illumination via the surgical instrument is turned off at time $t_7$. Accordingly, system 100 may infer that the decrease in temperature of the surgical instrument is due to the decrease in illumination output by the surgical instrument. Accordingly, system 100 does not determine that the surgical instrument is in physical contact with patient tissue at time $t_8$.

As another example, system 100 may determine that the temperature of the surgical instrument changes from a first temperature at time $t_4$ to a second temperature at time $t_5$ that varies from the first temperature by more than a predetermined amount. Additionally, system 100 may further determine that the surgical instrument has moved immediately prior to the change of the temperature (e.g., at or immediately prior to time $t_4$). Accordingly, system 100 may determine that, because the change in temperature has occurred immediately after movement of the surgical instrument, the surgical instrument is in physical contact with patient tissue at time $t_5$.

As mentioned, system 100 may determine, based on the tracked temperature of the surgical instrument, that the surgical instrument is in physical contact with patient tissue when the temperature of the surgical instrument changes from a first temperature to a second temperature that varies from the first temperature by at least a predetermined amount. In some examples the predetermined amount may vary based on the tracked operations of the surgical instrument. For instance, the predetermined amount may be decreased when the tracked operations of the surgical instrument suggest that physical contact with patient tissue is likely (e.g., movement prior to the change in temperature, an increased intensity of reflected illumination detected by an imaging device, increased saturation in the imaging device, surgical instrument sensor data indicating contact with another object, etc.). Similarly, the predetermined amount may be increased when the tracked operations of the surgical instrument indicate that physical contact with patient tissue is not likely (e.g., no movement of the surgical instrument, a decreased intensity of reflected illumination detected by an imaging device, decreased brightness of an imaged captured by the imaging device, detection of a collision of the surgical instrument with another surgical instrument, etc.).

In the foregoing embodiments the surgical instrument has been described as having a non-contact state temperature above the patient tissue temperature, and thus system 100 detects physical contact with patient tissue when the temperature of the surgical instrument decreases. In like manner the systems and methods described herein also apply to a surgical instrument that has a non-contact state temperature below the patient tissue temperature. In such cases system 100 detects physical contact with patient tissue when the temperature of the surgical instrument increases.

The preceding examples provide various exemplary methods and criteria for determining, based on a tracked temperature of a surgical instrument and/or based on tracked operations of the surgical instrument, that the surgical instrument is in physical contact with patient tissue. However, system 100 is not limited to the specific methods and criteria described in the examples above, but may include variations and modifications of the methods and criteria as may suit a particular implementation. Additionally, system 100 may utilize any combination or sub-combination of methods and criteria for determining that the surgical instrument is in physical contact with patient tissue. System 100 may combine various methods and criteria in any suitable way that facilitates system 100 discerning when the surgical instrument is in physical contact with patient tissue.

As mentioned above, system 100 may be configured to perform, in response to a determination that the surgical instrument is in physical contact with patient tissue, a mitigation operation configured to mitigate the physical contact of the surgical instrument with the patient tissue. Mitigation operations include any operations configured to reduce the likelihood of injury to patient tissue caused by the physical contact of the surgical instrument with the patient tissue. In some examples system 100 performs a mitigation operation by directing the surgical instrument and/or a surgical system associated with the surgical instrument to perform another mitigation operation.

In some examples mitigation operations include any suitable operations configured to notify an operator of the surgical instrument that the surgical instrument s in physical contact with patient tissue. For example, system 100 may direct surgical system 206 to present a notification that the surgical instrument is in physical contact with patient tissue. The notification may be in any format, such as but not limited to visual (e.g., a warning light, a warning icon displayed on a graphical user interface viewed by a user, a message displayed on the graphical user interface, etc.), audio (e.g., a warning tone, an audible warning message, etc.), and haptic (e.g., vibration of a manual controller of the surgical instrument, etc.). Additionally, the notification may be provided by any suitable device, including but not limited to a display device included in surgical system 206 (e.g., a stereo viewer in a surgeon console, an auxiliary display device, a mobile device associated with a user, etc.), a speaker (e.g., a speaker included in the surgeon console, a speaker on a mobile device, etc.), a manual control device (e.g., a controller for manually controlling operation of the surgical instrument, etc.), and the like.

Figure 6:
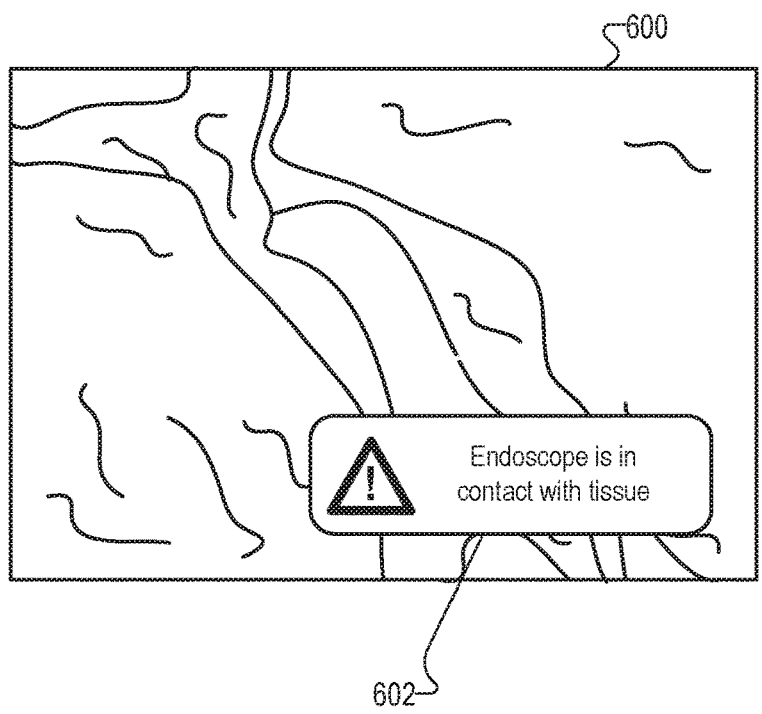
FIGS. 6-8 illustrate exemplary notifications of tissue contact that may be presented by way of a display device according to principles described herein.

FIG. 6 illustrates an exemplary notification that may be presented to a user (e.g., a surgeon, a technician, etc.). As shown, an image 600 presented by an image display system included in a surgical system (e.g., surgical system 206) shows an endoscopic view of a surgical area as captured by an endoscope. Image 600 includes a message bubble 602 superimposed on the endoscopic view of the surgical area. As shown, message bubble 602 includes a message that states: "Endoscope is in contact with tissue," It will be appreciated that message bubble 602 may be positioned at any location and may provide any information as may suit a particular implementation. In some examples message bubble 602 may include a selectable option (not shown) configured to dismiss or minimize message bubble 602 upon selection by the user. As is evident from FIG. 6, system 100 is configured to detect when a surgical instrument (e.g., an endoscope) included in a surgical system is in physical contact with patient tissue located outside of an endoscopic field of view during a minimally-invasive surgical procedure.

In situations where multiple surgical instruments are located at the surgical area, the notification may identify the particular surgical instrument that is in physical contact with patient tissue. In some examples a warning message may name the particular surgical instrument that is in physical contact with patient tissue (see, e.g., FIG. 6). Additionally or alternatively, an endoscopic image may graphically identify (e.g., highlight, point to, mark with an icon, etc.) the particular surgical instrument. The particular surgical instrument that is in physical contact with patient tissue may be identified in any suitable way. In some examples system 100 may obtain (e.g., from the surgical instrument that is in physical contact with patient tissue) an ID of the surgical instrument and provide the ID of the surgical instrument to the surgical system. The surgical system may track the location of the surgical instruments located at the surgical area (e.g.; utilizing kinematic data, marker-based computer vision tracking, image object recognition, etc.) and, based on the ID of the surgical instrument, identify the particular surgical instrument that is in physical contact with patient tissue.

Figure 7:
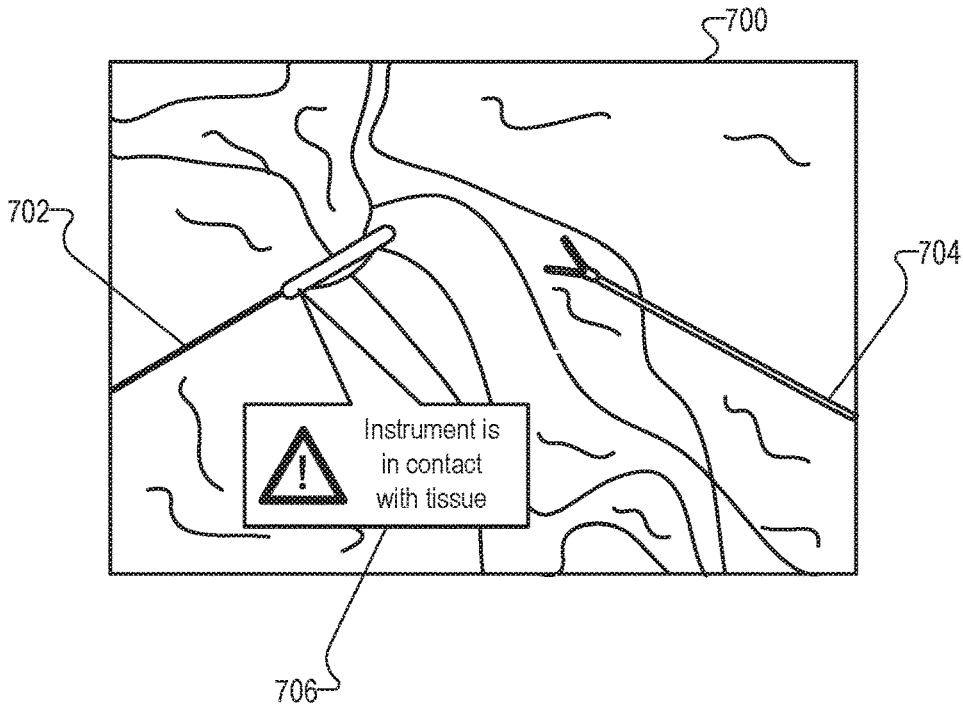

FIG. 7 illustrates an exemplary notification that may be presented to a user to identify the particular surgical instrument that is in physical contact with patient tissue. As shown, an image 700 presented by way of an image display system included in a surgical system (e.g., surgical system 206) shows an endoscopic view of a surgical area as captured by an endoscope, including a view of an ultrasound instrument 702 and a scissors instrument 704. When system 100 determines that ultrasound instrument 702 is in physical contact with patient tissue a message bubble 706 is displayed on the endoscopic view of the surgical area and points to ultrasound instrument 702. As shown in FIG. 7, message bubble 706 includes a message that states: "Instrument is in contact with tissue." It will be appreciated that message bubble 706 may be positioned at any location and may provide any information as may suit a particular implementation, With this configuration a user may quickly identify which surgical instrument is in physical contact with patient tissue and take corrective action. Additionally, since ultrasound instrument 702 must be in physical contact with patient tissue in order to capture and generate ultrasound images, the features described herein may help the user to know when ultrasound instrument 702 is in physical contact with patient tissue.

In examples where system 100 identifies a particular location on the surgical instrument that is in physical contact with patient tissue, the notification may show or identify the location on the surgical instrument that is in physical contact with patient tissue. The particular location on the surgical instrument that is in physical contact with patient tissue may be identified in any suitable way. As mentioned above, system 100 may use the tracked temperature of each location on the surgical instrument to determine the particular location on the surgical instrument that is in physical contact with patient tissue. System 100 may provide to a surgical system (e.g., surgical system 206) information identifying the particular location. As also mentioned above, the surgical system may track the location of the surgical instrument within the surgical area. Based on the tracked location of the surgical instrument and the particular location on the surgical instrument, the surgical system may configure the notification to identify the particular location on the surgical instrument that is in physical contact with patient tissue.

Figure 8:
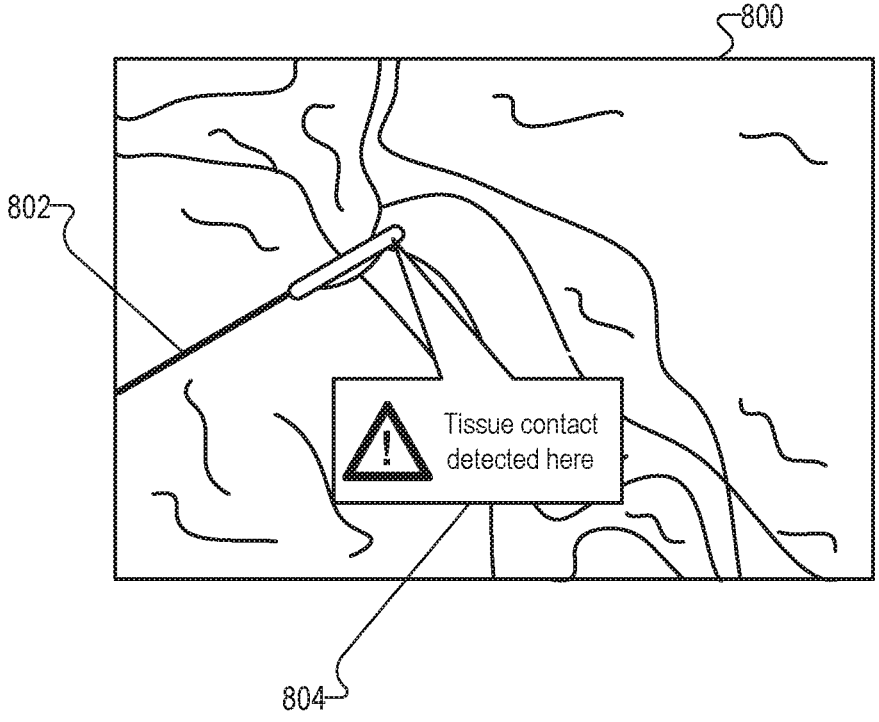

FIG. 8 illustrates an exemplary notification that may be presented to a user to identify the particular location on the surgical instrument that is in physical contact with patient tissue. As shown, an image 800 presented by way of an image display system included in a surgical system (e.g., surgical system 206) shows an endoscopic view of a surgical area as captured by an endoscope, including a view of an ultrasound instrument 802 located at the surgical area. When system 100 determines that a distal end region of ultrasound instrument 802 is in physical contact with patient tissue a message bubble 804 is displayed on the endoscopic view of the surgical area and points to the distal end region of ultrasound instrument 802. As shown, a message in message bubble 804 states: "Tissue contact detected here." It will be appreciated that message bubble 804 may be positioned at any location and may provide any information as may suit a particular implementation.

Additionally or alternatively to notifications, mitigation operations may include any operations configured to decrease the temperature of the surgical instrument and thereby reduce the risk of injury to the patient tissue. To this end, system 100 may adjust, or direct the surgical instrument and/or a surgical system associated with the surgical instrument to adjust, the operation of the surgical instrument. For example, where surgical instrument 202 is implemented by an imaging device (e.g., an endoscope), system 100 may direct surgical system 206 to adjust the output of illumination provided to the surgical area by way of surgical instrument 202. The output of illumination may be adjusted, for example, by decreasing an intensity of light provided to the surgical instrument, intermittently discontinuing the output of light provided to the surgical instrument, or turning off a light source (e.g., fluorescence excitation illumination source, a blue light source, etc.). As another example, system 100 may direct surgical system 206 to adjust the operation of an imaging device (e.g., decrease resolution, decrease frame rate, etc.) to thereby reduce heat generated by the imaging device. In other examples system 100 may direct surgical system 206 to decrease the amount of passive heat applied to the surgical instrument, increase cooling of the surgical instrument, decrease an amount of energy (e.g., cauterizing energy) provided by way of the surgical instrument, and the like.

FIG. 9 illustrates an exemplary method 900 of performing mitigation operations. While FIG. 9 illustrates exemplary operations according to one embodiment, other embodiments may omit, add to, reorder, and/or modify any of the operations shown in FIG. 9.

In operation 902, system 100 determines whether a surgical instrument is in physical contact with patient tissue. Operation 902 may be performed in any of the ways described herein. If system 100 does not determine that the surgical instrument is in physical contact with patient tissue, system 100 returns to the start and continues monitoring for tissue contact. However, if system 100 determines that the surgical instrument is in physical contact with patient tissue, system 100 proceeds to operation 904.

In operation 904 system 100 checks whether a predetermined amount of time has elapsed since the tissue contact was first detected. The predetermined amount of time may be any time period as may suit a particular implementation (e.g., 2 minutes). In some examples the predetermined amount of time is set by system 100. Additionally or alternatively, the predetermined amount of time is configurable by a user. If system 100 determines that the predetermined amount of time has not elapsed since the tissue contact was first detected, system 100 proceeds to operation 906. In operation 906 system 100 presents, or directs the surgical system to present, a notification that the surgical instrument is in physical contact with patient tissue. Operation 906 may be performed in any of the ways described herein.

If, however, system 100 determines that the predetermined amount of time has elapsed since the tissue contact was first detected, system 100 proceeds to operation 908. In operation 908 system 100 adjusts, or directs the surgical system to adjust, an operation of the surgical instrument to mitigate the physical contact of the surgical instrument with the patient tissue. Operation 908 may be performed in any of the ways described herein.

After operation 906 and operation 908 system 100 returns to operation 902 to determine if the surgical instrument is still in physical contact with patient tissue. If system 100 determines that the surgical instrument is no longer in physical contact with patient tissue system 100 returns to the start to monitor for physical contact with patient tissue. System 100 may also dismiss, or direct the surgical system to dismiss, the notification and/or resume, or direct the surgical system to resume, normal operation of the surgical instrument.

In method 900 a notification that the surgical instrument is in physical contact with patient tissue is presented, but operation of the surgical instrument is not adjusted unless a predetermined amount of time has elapsed. In this way system 100 may allow a user to perform an action to mitigate the tissue contact before the surgical system automatically performs operations to mitigate the tissue contact. However, the processing for performing mitigation operations is not limited to the foregoing sequence. In alternative embodiments system 100 may be configured to present, or direct the surgical system to present, the notification only after the surgical instrument has remained in physical contact with the patient tissue for another predetermined amount of time (e.g., three minutes). In such embodiments it may be presumed that physical contact with patient tissue is only temporary and that the surgical instrument will likely be moved before the patient tissue is injured. In other alternative embodiments system 100 may be configured to provide, or direct the surgical system to provide, the notification and adjust, or direct the surgical system to adjust, the operation of the surgical instrument simultaneously. In yet further embodiments any predetermined amounts of time and/or the order of performing mitigation operations may be set based on the type of surgical instrument. For instance, for an endoscope that operates at a higher non-contact state temperature than a scissors instrument, the predetermined amount of time considered in operation 904 may be set shorter for the endoscope than for the scissors instrument.

Figure 10:
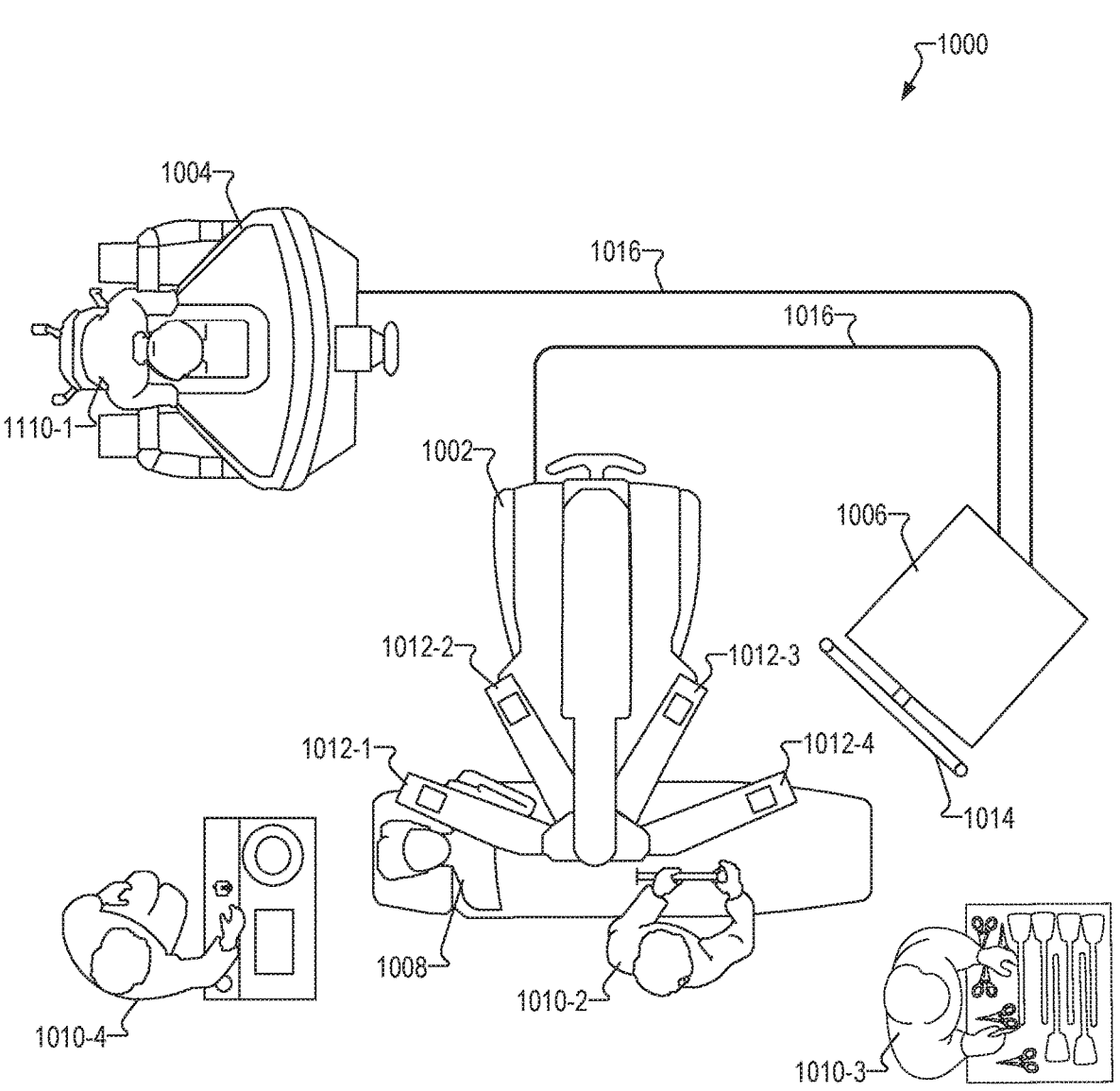
FIG. 10 illustrates an exemplary computer-assisted surgical system according to principles described herein.

FIG. 10 illustrates an exemplary computer-assisted surgical system 1000 ("surgical system 1000"). As described herein, system 100 may be implemented by surgical system 1000, implemented by a component included in surgical system 1000, connected to surgical system 1000, and/or otherwise used in conjunction with surgical system 1000.

As shown, surgical system 1000 may include a manipulating system 1002, a user control system 1004, and an auxiliary system 1006 communicatively coupled one to another, Surgical system 1000 may be utilized by a surgical team to perform a computer-assisted surgical procedure on a patient 1008. As shown, the surgical team may include a surgeon 1010-1, an assistant 1010-2, a nurse 1010-3, and an anesthesiologist 1010-4, all of whom may be collectively referred to as "surgical team members 1010." Additional or alternative surgical team members may be present during a surgical session as may serve a particular implementation.

While FIG. 10 illustrates an ongoing minimally invasive surgical procedure, it will be understood that surgical system 1000 may similarly be used to perform open surgical procedures or other types of surgical procedures that may similarly benefit from the accuracy and convenience of surgical system 1000. Additionally, it will be understood that the surgical session throughout which surgical system 1000 may be employed may not only include an operative phase of a surgical procedure, as is illustrated in FIG. 10, but may also include preoperative, postoperative, and/or other suitable phases of the surgical procedure.

As shown in FIG. 10, manipulating system 1002 may include a plurality of manipulator arms 1012 (e.g., manipulator arms 1012-1 through 1012-4) to which a plurality of surgical instruments may be coupled. While manipulating system 1002 is depicted and described herein as including four manipulator arms 1012, it will be recognized that manipulating system 1002 may include only a single manipulator arm 1012 or any other number of manipulator arms as may serve a particular implementation.

Manipulator arms 1012 and/or surgical instruments attached to manipulator arms 1012 may include one or more displacement transducers, orientational sensors, and/or positional sensors used to generate raw (i.e., uncorrected) kinematics information. One or more components of surgical system 1000 may be configured to use the kinematics information to track (e.g., determine positions and orientations of) and/or control the surgical instruments. Additionally, surgical instruments attached to manipulator arms 1012 may include one or more temperature sensors used to generate temperature data. System 100 may be configured to use the temperature data to track the temperature of the surgical instruments during the surgical session.

User control system 1004 may be configured to facilitate control by surgeon 1010-1 of manipulator arms 1012 and surgical instruments attached to manipulator arms 1012. For example, surgeon 1010-1 may interact with user control system 1004 to remotely move or manipulate manipulator arms 1012 and the surgical instruments. To this end, user control system 1004 may provide surgeon 1010-1 with images (e.g., high-definition 3D images, composite medical images, etc.), such as images 600, 700, and/or 800, of a surgical area associated with patient 1008 as captured by an imaging system (e.g., an endoscope implemented by surgical instrument 202). In certain examples, user control system 1004 may include a stereo viewer having two displays where stereoscopic images of a surgical area associated with patient 1008 and generated by a stereoscopic imaging system may be viewed by surgeon 1010-1. Surgeon 1010-1 may utilize the images to perform one or more procedures with one or more surgical instruments attached to manipulator arms 1012.

To facilitate control of surgical instruments, user control system 1004 may include a set of master controls. These master controls may be manipulated by surgeon 1010-1 to control movement of surgical instruments (e.g., by utilizing robotic and/or teleoperation technology). The master controls may be configured to detect a wide variety of hand, wrist, and finger movements by surgeon 1010-1. In this manner, surgeon 1010-1 may intuitively perform a procedure using one or more surgical instruments.

Auxiliary system 1006 may include one or more computing devices configured to perform primary processing operations of surgical system 1000. In such configurations, the one or more computing devices included in auxiliary system 1006 may control and/or coordinate operations performed by various other components (e.g., manipulating system 1002 and user control system 1004) of surgical system 1000. For example, a computing device included in user control system 1004 may transmit instructions to manipulating system 1002 by way of the one or more computing devices included in auxiliary system 1006. As another example, auxiliary system 1006 may receive, from manipulating system 1002, and process image data representative of images (e.g., images 600, 700, and/or 800) captured by an imaging device attached to one of manipulator arms 1012.

In some examples, auxiliary system 1006 may be configured to present visual content to surgical team members 1010 who may not have access to the images provided to surgeon 1010-1 at user control system 1004. To this end, auxiliary system 1006 may include a display monitor 1014 configured to display one or more user interfaces, such as images (e.g., 2D images, composite medical images, etc.) of the surgical area, information associated with patient 1008 and/or the surgical procedure, and/or any other visual content as may serve a particular implementation. For example, display monitor 1014 may display images of the surgical area together with additional content (e.g., graphical content, contextual information, etc.) concurrently displayed with the images. In some embodiments, display monitor 1014 is implemented by a touchscreen display with which surgical team members 1010 may interact (e.g., by way of touch gestures) to provide user input to surgical system 1000.

Manipulating system 1002, user control system 1004, and auxiliary system 1006 may be communicatively coupled one to another in any suitable manner. For example, as shown in FIG. 10, manipulating system 1002, user control system 1004, and auxiliary system 1006 may be communicatively coupled by way of control lines 1016, which may represent any wired or wireless communication link as may serve a particular implementation. To this end, manipulating system 1002, user control system 1004, and auxiliary system 1006 may each include one or more wired or wireless communication interfaces, such as one or more local area network interfaces, Wi-Fi network interfaces, cellular interfaces, etc.

Figure 11:
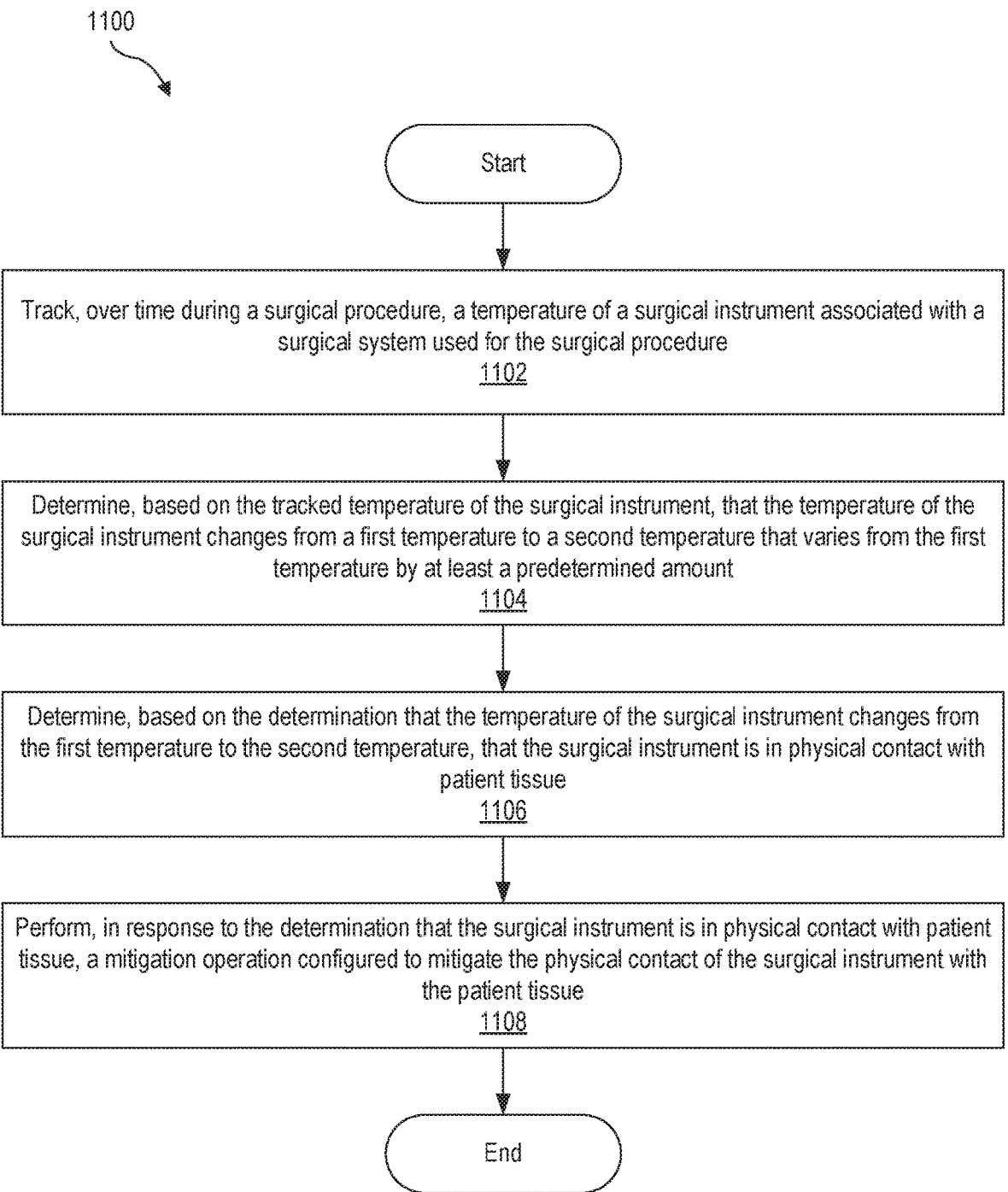
FIG. 11 illustrates an exemplary method of detecting physical contact of a surgical instrument with patient tissue according to principles described herein.

FIG. 11 shows an exemplary method 1100 of detecting physical contact of a surgical instrument with patient tissue. While FIG. 11 illustrates exemplary operations according to one embodiment, other embodiments may omit, add to, reorder, combine, and/or modify any of the steps shown in FIG. 11. One or more of the operations shown in in FIG. 11 may be performed by system 100, any components included therein, and/or any implementation thereof.

In operation 1102, a tissue contact detection system tracks, over time during a surgical procedure, a temperature of a surgical instrument associated with a surgical system used for the surgical procedure. Operation 1102 may be performed in any of the ways described herein.

In operation 1104, the tissue contact detection system determines, based on the tracked temperature of the surgical instrument, that the temperature of the surgical instrument changes from a first temperature to a second temperature that varies from the first temperature by at least a predetermined amount. Operation 1104 may be performed in any of the ways described herein.

In operation 1106, the tissue contact detection system determines, based on the determination that the temperature of the surgical instrument changes from the first temperature to the second temperature, that the surgical instrument is in physical contact with patient tissue. Operation 1106 may be performed in any of the ways described herein.

In operation 1108, the tissue contact detection system performs, in response to the determination that the surgical instrument is in physical contact with patient tissue, a mitigation operation configured to mitigate the physical contact of the surgical instrument with the patient tissue. Operation 1108 may be performed in any of the ways described herein.

In some examples, a non-transitory computer-readable medium storing computer-readable instructions may be provided in accordance with the principles described herein. The instructions, when executed by a processor of a computing device, may direct the processor and/or computing device to perform one or more operations, including one or more of the operations described herein. Such instructions may be stored and/or transmitted using any of a variety of known computer-readable media.

A non-transitory computer-readable medium as referred to herein may include any non-transitory storage medium that participates in providing data (e.g., instructions) that may be read and/or executed by a computing device (e.g., by a processor of a computing device). For example, a non-transitory computer-readable medium may include, but is not limited to, any combination of non-volatile storage media and/or volatile storage media. Exemplary non-volatile storage media include, but are not limited to, read-only memory, flash memory, a solid-state drive, a magnetic storage device (e.g. a hard disk, a floppy disk, magnetic tape, etc.), ferroelectric random-access memory ("RAM"), and an optical disc (e.g., a compact disc, a digital video disc, a Blu-ray disc, etc.). Exemplary volatile storage media include, but are not limited to, RAM (e.g., dynamic RAM).

FIG. 12 illustrates an exemplary computing device 1200 that may be specifically configured to perform one or more of the processes described herein. Any of the systems, units, computing devices, and/or other components described herein may be implemented by computing device 1200.

As shown in FIG. 12, computing device 1200 may include a communication interface 1202, a processor 1204, a storage device 1206, and an input/output ("I/O") module 1208 communicatively connected one to another via a communication infrastructure 1210. While an exemplary computing device 1200 is shown in FIG. 12, the components illustrated in FIG. 12 are not intended to be limiting. Additional or alternative components may be used in other embodiments. Components of computing device 1200 shown in FIG. 12 will now be described in additional detail.

Communication interface 1202 may be configured to communicate with one or more computing devices. Examples of communication interface 1202 include, without limitation, a wired network interface (such as a network interface card), a wireless network interface (such as a wireless network interface card), a modem, an audio/video connection, and any other suitable interface.

Processor 1204 generally represents any type or form of processing unit capable of processing data and/or interpreting, executing, and/or directing execution of one or more of the instructions, processes, and/or operations described herein. Processor 1204 may perform operations by executing computer-executable instructions 1212 (e.g., an application, software, code, and/or other executable data instance) stored in storage device 1206.

Storage device 1206 may include one or more data storage media, devices, or configurations and may employ any type, form, and combination of data storage media and/or device. For example, storage device 1206 may include, but is not limited to, any combination of the non-volatile media and/or volatile media described herein. Electronic data, including data described herein, may be temporarily and/or permanently stored in storage device 1206. For example, data representative of computer-executable instructions 1212 configured to direct processor 1204 to perform any of the operations described herein may be stored within storage device 1206. In some examples, data may be arranged in one or more databases residing within storage device 1206.

I/O module 1208 may include one or more I/O modules configured to receive user input and provide user output. I/O module 1208 may include any hardware, firmware, software, or combination thereof supportive of input and output capabilities. For example, I/O module 1208 may include hardware and/or software for capturing user input, including, but not limited to, a keyboard or keypad, a touchscreen component (e.g., touchscreen display), a receiver (e.g., an RF or infrared receiver), motion sensors, and/or one or more input buttons.

I/O module 1208 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O module 1208 is configured to provide graphical data to a display for presentation to a user. The graphical data may be representative of one or more graphical user interfaces and/or any other graphical content as may serve a particular implementation.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:
a memory storing instructions; and
a processor communicatively coupled to the memory and configured to execute the instructions to:
  track, over time during a surgical session, a temperature of a surgical instrument associated with a surgical system used for the surgical session,
  track, over time during the surgical session, movement of the surgical instrument based on kinematic data associated with the surgical system,
  determine, based on the tracked movement of the surgical instrument, that the surgical instrument has moved,
  determine, based on the tracked temperature of the surgical instrument, that the temperature of the surgical instrument changes from a first temperature to a second temperature that varies from the first temperature by at least a predetermined amount,
  determine, based on the determination that the temperature of the surgical instrument changes from the first temperature to the second temperature and the determination that the surgical instrument has moved, that the surgical instrument is in physical contact with patient tissue, and
  perform a mitigation operation in response to the determination that the surgical instrument is in physical contact with patient tissue.

2. The system of claim 1, wherein:
the processor is further configured to execute the instructions to determine that the temperature of the surgical instrument changes from the first temperature to the second temperature by at least a predetermined rate of change or within a predetermined time interval, and
the determining that the surgical instrument is in physical contact with patient tissue is further based on the determination that the temperature of the surgical instrument changes from the first temperature to the second temperature by at least the predetermined rate of change or within the predetermined time interval.

3. The system of claim 1, wherein:
the processor is further configured to execute the instructions to determine that the second temperature is within a predetermined contact-state temperature range, and
the determining that the surgical instrument is in the physical contact with the patient tissue is further based on the determination that the second temperature is within the predetermined contact-state temperature range.

4. The system of claim 1, wherein:
the processor is further configured to execute the instructions to track, over time during the surgical session, operations of the surgical instrument, and
the determining that the surgical instrument is in physical contact with patient tissue is further based on the tracked operations of the surgical instrument.

5. The system of claim 1, wherein:
the processor is further configured to execute the instructions to:
  determine, based on the tracked movement of the surgical instrument, that the surgical instrument has moved immediately prior to the change of the temperature of the surgical instrument from the first temperature to the second temperature, and
the determining that the surgical instrument is in physical contact with patient tissue is further based on the determination that the surgical instrument has moved immediately prior to the change of the temperature of the surgical instrument from the first temperature to the second temperature.

6. The system of claim 1, wherein the processor is further configured to execute the instructions to maintain a non-contact state temperature of the surgical instrument at a predetermined level.

7. The system of claim 1, wherein the processor is further configured to execute the instructions to:

determine that a non-contact state temperature of the surgical instrument varies from a temperature of the patient tissue by less than another predetermined amount, and direct, in response to the determination that the non-contact state temperature varies from the temperature of the patient tissue by less than the another predetermined amount, the surgical system to increase or decrease the non-contact state temperature of the surgical instrument such that the non-contact state temperature of the surgical instrument varies from the temperature of the patient tissue by at least the another predetermined amount.

8. The system of claim 1, wherein at least one of the first temperature and the second temperature is in a steady-state.

9. The system of claim 1, wherein:

the surgical instrument comprises an endoscope, and the mitigation operation further comprises adjusting illumination output from a distal end of the endoscope.

10. The system of claim 1, wherein the mitigation operation further comprises decreasing an amount of passive heat added to the surgical instrument.

11. The system of claim 1, wherein the tracking of the temperature of the surgical instrument comprises receiving, over time from a temperature sensor on the surgical instrument, temperature data representative of the temperature of the surgical instrument.

12. The system of claim 1, wherein:

the tracking of the temperature of the surgical instrument comprises receiving, over time from a plurality of temperature sensors located at a plurality of locations on the surgical instrument, temperature data representative of the temperature of the surgical instrument at each of the plurality of locations, the processor is further configured to execute the instructions to identify, based on the temperature data, a location on the surgical instrument that is in physical contact with patient tissue, and the mitigation operation comprises providing a notification of the location on the surgical instrument that is in physical contact with patient tissue.

13. A method performed by a tissue contact system comprising memory storing instructions and a processor communicatively coupled to the memory and configured to execute the instructions to perform the method, the method comprising:

tracking over time during a surgical session, a temperature of a surgical instrument included in a surgical system used for the surgical session;

tracking over time during the surgical session, movement of the surgical instrument based on kinematic data associated with the surgical system;

determining based on the tracked movement of the surgical instrument, that the surgical instrument has moved;

determining based on the tracked temperature of the surgical instrument, that the temperature of the surgical instrument changes from a first temperature to a second temperature that varies from the first temperature by at least a predetermined amount;

determining based on the determination that the temperature of the surgical instrument changes from the first temperature to the second temperature and the determination that the surgical instrument has moved, that the surgical instrument is in physical contact with patient tissue; and performing a mitigation operation in response to the determination that the surgical instrument is in physical contact with patient tissue.

14. The method of claim 13, further comprising:

determining that the temperature of the surgical instrument changes from the first temperature to the second temperature by at least a predetermined rate of change or within a predetermined time interval, wherein the determining that the surgical instrument is in physical contact with patient tissue is further based on the determination that the temperature of the surgical instrument changes from the first temperature to the second temperature by at least the predetermined rate of change or within the predetermined time interval.

15. The method of claim 13, further comprising:

determining that the second temperature is within a predetermined contact-state temperature range, wherein the determining that the surgical instrument is in physical contact with patient tissue is further based on the determination that the second temperature is within the predetermined contact-state temperature range.

16. The method of claim 13, further comprising:

tracking over time during the surgical session, operations of the surgical instrument, wherein the determining that the surgical instrument is in physical contact with patient tissue is further based on the tracked operations of the surgical instrument.

17. The method of claim 13, further comprising:

determining based on the tracked movement of the surgical instrument, that the surgical instrument has moved immediately prior to the change of the temperature of the surgical instrument from the first temperature to the second temperature, wherein the determining that the surgical instrument is in physical contact with patient tissue is further based on the determination that the surgical instrument has moved immediately prior to the change of the temperature of the surgical instrument from the first temperature to the second temperature.

* * * * *